United States Patent

Mikami et al.

Patent Number: 5,155,240
Date of Patent: Oct. 13, 1992

[54] PROCESS FOR PRODUCING OPTICALLY ACTIVE DIHYDROPYRAN DERIVATIVE

[75] Inventors: Koichi Mikami, Kanagawa; Masahiro Terada, Tokyo; Takeshi Nakai; Noboru Sayo, both of Kanagawa, all of Japan

[73] Assignee: Takasago International Corporation, Tokyo, Japan

[21] Appl. No.: 668,656

[22] Filed: Mar. 13, 1991

[30] Foreign Application Priority Data

Sep. 5, 1990 [JP] Japan ................................. 2-235102
Jan. 8, 1991 [JP] Japan ................................. 3-11580

[51] Int. Cl.⁵ .......................................... C07D 309/06
[52] U.S. Cl. .................................. 549/425; 549/424; 549/420; 549/419; 549/417; 549/405; 549/404; 549/399; 549/396; 549/355; 549/214
[58] Field of Search ................. 549/425, 424, 420, 419, 549/417, 405, 404, 399, 396, 355, 214

[56] References Cited

PUBLICATIONS

Terada et al., Lecture Preprint II, 59th Spring Annual Meeting of Chemical Society of Japan, p. 1356 (Mar. 14, 1990).
Tetrahedron, vol. 32, pp. 2957–2959 (1976).
J. Org. Chem., pp. 1440–1456 (1985).
Tetrahedron, vol. 42, pp. 2787–2801 (1986).
J. Chem. Soc., Chem. Commun., pp. 676–677 (1987).
Synthesis, pp. 544–545 (1987).
J. Chem. Soc., Chem. Commun., pp. 540–542 (1983).

Primary Examiner—Nicky Chan
Attorney, Agent, or Firm—Sughrue, Mion, Zinn, Macpeak & Seas

[57] ABSTRACT

A process for producing an optically active dihydropyran derivative represented by formula (1):

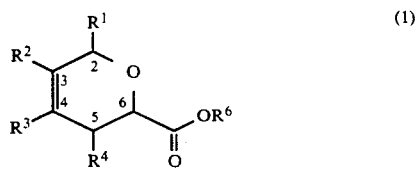

wherein $R^1$, $R^2$, $R^3$, and $R^4$ each represents a hydrogen atom, a lower alkyl group, a tri-lower alkylsilylmethyl group, a lower alkoxycarbonylamino group, or an $-OR^5$ group, wherein $R^5$ represents a lower alkyl group, a lower acyl group, a lower alkoxycarbonyl group, a di-lower alkylcarbamoyl group, or a tri-lower alkylsilyl group, or $R^1$ and $R^2$ are taken together to form a 5- to 7-membered cyclic hydrocarbon group or to form a condensed heterocyclic group with an oxygen atom, or $R^2$ and $R^3$ are taken together to form a 5- to 7-membered cyclic hydrocarbon group or to form a condensed heterocyclic group with an oxygen atom, provided that all of $R^1$, $R^2$, $R^3$, and $R^4$ do not represent hydrogen atoms at the same time; and $R^6$ represents a lower alkyl group, which comprises reacting a diene compound represented by formula (2):

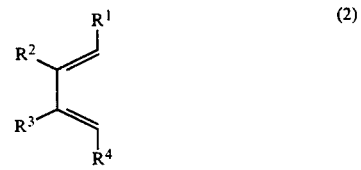

wherein $R^1$, $R^2$, $R^3$, and $R^4$ have the same meanings as defined above, with a glyoxylic acid ester represented by formula (3):

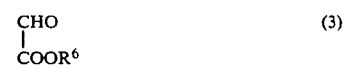

wherein $R^6$ has the same meaning as defined above, in the presence of a binaphthol-titanium complex represented by formula (4):

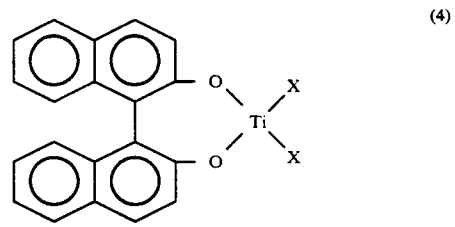

wherein X represents a chlorine atom or a bromine atom, is disclosed.

3 Claims, No Drawings

PROCESS FOR PRODUCING OPTICALLY ACTIVE DIHYDROPYRAN DERIVATIVE

FIELD OF THE INVENTION

The present invention relates to a process for producing an optically active dihydropyran derivative represented by formula (1):

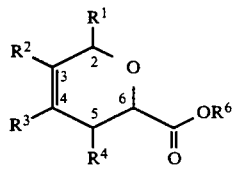

wherein $R^1$, $R^2$, $R^3$, and $R^4$ each represents a hydrogen atom, a lower alkyl group, a tri-lower alkylsilylmethyl group, a lower alkoxycarbonylamino group, or an $-OR^5$ group, wherein $R^5$ represents a lower alkyl group, a lower acyl group, a lower alkoxycarbonyl group, a di-lower alkylcarbamoyl group, or a tri-lower alkylsilyl group, or $R^1$ and $R^2$ are taken together to form a 5- to 7-membered cyclic hydrocarbon group or to form a condensed heterocyclic group with an oxygen atom, or $R^2$ and $R^3$ are taken together to form a 5- to 7-membered cyclic hydrocarbon group or to form a condensed heterocyclic group with an oxygen atom, provided that all of $R^1$, $R^2$, $R^3$, and $R^4$ do not represent hydrogen atoms at the same time; and $R^6$ represents a lower alkyl group.

BACKGROUND OF THE INVENTION

Optically active dihydropyran derivatives represented by formula (1) are useful compounds, for example, as intermediates for syntheses of the saccharides described in A. KONOWAL et al., *Tetrahedron*, Vol. 32, pp. 2957-2959 (1976) or of the antibiotics described in K. C. Nicolaou et al., *J. Org. Chem.*, pp. 1440 (1985) and STEVEN D. BURKE et al., *Tetrahedron*, Vol. 42, pp. 2787-2801 (1986).

Hitherto, as processes for producing such optically active dihydropyran derivatives of formula (1), a process in which 1-methoxy-1,3-butadiene or 1,3-pentadiene is reacted with a glyoxylic acid ester in the presence of a catalyst which is menthoxyaluminum dichloride or Eu(hfc)$_3$, i.e., europium (III) tris[3-heptafluoropropyl-hydroxymethylene)-(+)-camphorate] has been reported in M. Quimpère et al., *J. Chem. Soc., Chem. Commun.*, pp. 676-677 (1987).

However, the above-described known process has the following drawbacks. The optically active site in each of the catalysts to be used in the process has a specific absolute configuration derived from a naturally occurring raw material, that is, absolute configurations for menthoxyaluminum dichloride and Eu(hfc)$_3$ are derived from (−)-menthol and (+)-camphor, respectively. However, even when products respectively having the absolute configurations corresponding to those of the two catalysts are intended to be obtained, the menthoxyaluminum dichloride catalyst cannot yield a desired product having an industrially utilizable optical purity. Hence, it has virtually been possible to produce only products having a specific absolute configuration obtained from the Eu(hfc)$_3$ catalyst derived from (+)-camphor. In addition, even with the Eu(hfc)$_3$ catalyst, attainable optical purities of the products are 64% ee at maximum, which value is attained with (2R,6S)-2-methoxy-6-methoxycarbonyldihydropyran. It has, therefore, been desired to develop a process for producing a dihydropyran derivative having an even higher optical purity.

SUMMARY OF THE INVENTION

Under these circumstances, the present inventors have conducted intensive studies in order to overcome the above-described problems. As a result, it has now been found that a dihydropyran derivative having a high optical purity can be obtained efficiently with use of an optically active binaphthol-titanium complex as a catalyst. The present invention has been completed based on this finding.

Accordingly, an object of the present invention is to provide a process for producing a dihydropyran derivative represented by formula (1) given above.

Other objects and effects of the present invention will be apparent from the following description.

DETAILED DESCRIPTION OF THE INVENTION

The process of the present invention is illustrated by the following reaction scheme:

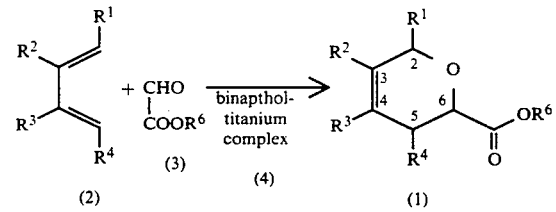

wherein $R^1$, $R^2$, $R^3$, $R^4$, and $R^6$ are as defined hereinabove.

That is, in the process of the present invention, a diene compound (2) is reacted with a glyoxylic acid ester (3) in the presence of a binaphthol-titanium complex (4) to produce an optically active dihydropyran derivative (1).

Substituents $R^1$, $R^2$, $R^3$, and $R^4$ in the diene compound (2) used as a raw material in the present invention each represents a hydrogen atom, a lower alkyl group, a tri-lower alkylsilylmethyl group, a lower alkoxycarbonylamino group, or an $-OR^5$ group, wherein $R^5$ represents a lower alkyl group, a lower acyl group, a lower alkoxycarbonyl group, a di-lower alkylcarbamoyl group, or a tri-lower alkylsilyl group, or $R^1$ and $R^2$ are taken together to form a 5- to 7-membered cyclic hydrocarbon group or to form a condensed heterocyclic group with an oxygen atom, or $R^2$ and $R^3$ are taken together to form a 5- to 7-membered cyclic hydrocarbon group or to form a condensed heterocyclic group with an oxygen atom. The term "lower" as referred to herein means a carbon chain having from 1 to 4 carbon atoms, which may be branched. Although $R^1$, $R^2$, $R^3$, and $R^4$ represent the same or different substituent groups, the case that all of $R^1$, $R^2$, $R^3$, and $R^4$ represent hydrogen atoms at the same time is not preferred because the desired reaction does not proceed. Specific examples of the diene compound (2) include 2-methyl-1,3-butadiene, 2,4-hexadiene, 2,4-heptadiene, 3-methyl-2,4-hexadiene, 3,4-dimethyl-2,4-hexadiene, 2-trimethylsilylmethyl-1,3-butadiene, 1,4-di(ethoxycarbonylamino)-1,3-butadiene, 1-methoxy-1,3-butadiene, 2-methoxy-1,3-butadiene, 1-methoxy-1,3-pentadiene, 1-ethoxy-1,3-pentadiene, 2-ethoxy-1,3-pentadiene, 1-methoxy-2-methyl-1,3-pentadiene, 3-ethoxy-2,4-hexadiene, 3-t-butoxy-2,4-hexadiene, 1-methoxy-2,3-dimethyl-1,3-pentadiene, 3-ethoxy-4-methyl-2,4-hexadiene, 1-ethoxy-4-ethoxycarbonylamino-1,3-butadiene, 1,3-dimethoxy-1,3-butadiene, 1-t-butoxy-3-methoxy-1,3-butadiene, 2-acetoxy-1,3-pentadiene, 1-ethoxycarbonyloxy-1,3-butadiene, 2-methoxycarbonyloxy-1,3-butadiene, 1-acetoxy-3-methoxycarbonyloxy-1,3-butadiene, 2-acetoxy-1-propoxycarbonyloxy-1,3-butadiene, 1-dimethylaminocarbonyloxy-1,3-butadiene, 2-diethylaminocarbonyloxy-1,3-butadiene, 3-ethoxy-1-dimethylaminocarbonyloxy-1,3-butadiene, 1-ethoxy-2-diethylaminocarbonyloxy-1,3-butadiene, 1-t-butyldimethylsiloxy--1,3-butadiene, 3-trimethylsiloxy-2,4-pentadiene, 1-methoxy-3-trimethylsiloxy-1,3-butadiene, 3-butoxy-1-triisopropylsiloxy-1,3-butadiene, 1,4-dimethoxy-2-trimethylsiloxy-1,3-butadiene, 1'-methoxyethylene-1-cyclohexene, 3-ethylene-4,5-dihydropyran, and 1-methoxyethylene-2-methylenecyclohexane.

R$^6$ in the glyoxylic acid ester (3) which is another raw material represents a lower alkyl group. The term "lower" as referred to herein has the same meaning as defined above. Specific examples of the glyoxylic acid ester (3) include methyl glyoxylate, ethyl glyoxylate, isopropyl glyoxylate, and t-butyl glyoxylate. These glyoxylic acid esters may be produced, for example, by the method proposed by T. ROSS KELLY et al., *Synthesis*, pp. 544–545 (1972).

The optically active binaphthol-titanium complex used as a catalyst is represented by formula (4):

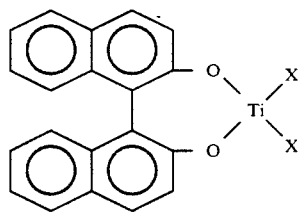

(4)

wherein X represents a chlorine atom or a bromine atom.

This binaphthol-titanium complex (4) can be prepared for example, by the method described in JP-A-2-40344. (The term "JP-A" as used herein means an "unexamined published Japanese patent application".) That is, a titanium tetrahalide (the halogen being chlorine or bromine) and tetraisopropoxytitanium are first mixed with each other in hexane to form crystals of a diisopropoxydihalogenotitanium, which are then dissolved in toluene. Meanwhile, a powder of molecular sieves 4A (a product on the market) is added to methylene chloride in an amount of at least 0.5 g per mmole of the catalyst. To this mixture are added the aboveprepared diisopropoxydihalogenotitanium toluene solution and then binaphthol. The resulting mixture is stirred for about 1 hour, thereby giving the binaphthol-titanium complex (4).

The binaphthol-titanium complex (4) includes an (R)-isomer and an (S)-isomer which are synthesized from (R)-binaphthol and (S)-binaphthol, respectively. These isomers can be suitably selected and used according to the desired absolute configuration for the optically active dihydropyran derivative (1) to be produced. Illustratively stated, in the case where the dihydropyran derivative to be obtained is the (R)-isomer with respect to the asymmetric carbon at the 6-position on the dihydropyran ring in formula (1), (R)-(4) can be used; in the case where the (S)-isomer is to be obtained, (S)-(4) can be used. Thus, according to the present invention, the absolute configuration of the carbon atom at the 6-position can be freely determined by suitably selecting the complex (4) to be used. In the case where substituent groups R$^1$ and/or R$^4$ is not a hydrogen atom, the carbon atom at the 2-position and/or the 5-position is also asymmetric. In this case, however, either the (R)-isomer or the (S)-isomer can be obtained in an advantageous proportion according to the absolute configuration for the complex (4).

In practicing the process of the present invention, the diene compound (2) and the glyoxylic acid ester (3) are added to a solution of the binaphthol-titanium complex (4) in an organic solvent, and then the mixture is allowed to react.

Examples of the organic solvent that can be used in the present invention include halogenated hydrocarbons such as methylene chloride, chloroform, and carbon tetrachloride; aromatic hydrocarbons such as benzene and toluene; and aprotic solvents such as tetrahydrofuran, diethyl ether, and dimethoxyethane.

The amount of the binaphthol-titanium complex catalyst used is generally in the range of from 0.001 to 1 mole, preferably from 0.01 to 0.1 mole, per mole of the raw materials (2) and (3), from the standpoint of obtaining the desired product in a high optical yield. The reaction temperature is generally in the range of from −50° C. to 0° C., preferably from −30° C. to −10° C. The reaction time is preferably from 1 to 20 hours.

After the reaction, an alkaline agent, e.g., a sodium hydrogencarbonate aqueous solution, is added to the reaction mixture. Subsequently, the resulting mixture is subjected to extraction with a solvent such as diethyl ether and ethyl acetate. After drying, the solvent is removed by evaporation, and the residue is purified by column chromatography with silica gel, etc., whereby the desired, optically active dihydropyran derivative (1) can be obtained in a high yield.

As described above, according to the process of the present invention, optically active dihydropyran derivatives with high optical purities can be produced from diene compounds and glyoxylates by use of an optically active binaphthol-titanium complex as a catalyst. Therefore, the process of the present invention is industrially advantageous.

The present invention will be explained in more detail with reference to the following Examples, which should not be construed to be limiting the scope of the invention.

In the Examples, the following analytical instruments were used for respective analyses.

$^1$H Nuclear Magnetic Resonance Spectroscopy (hereinafter abbreviated as $^1$H-NMR):
Type GEMINI 200 (200 MHz) (manufactured by Varian Co.) Measurement of Optical Rotation:
Polarimeter DIP-370 (manufactured by JASCO Ltd.)

EXAMPLE 1

Into a 50-ml Schlenk's tube which had been displaced by argon beforehand were introduced 2.98 ml (10 mmole) of tetraisopropoxytitanium and 5 ml of hexane and then 1.10 ml (10 mmole) of titanium tetrachloride. The mixture was stirred at room temperature for 10 minutes and then allowed to stand at room temperature for 3 hours, upon which white crystals precipitated. The solvent was taken out with a syringe, and 5 ml of hexane was added to the residue to recrystallize it. This procedure was repeated twice, and the resulting crystals were then dried under reduced pressure, thereby obtaining 3.09 g of white diisopropoxydichlorotitanium. 43 ml of toluene was added thereto to prepare a 0.3N solution.

On the other hand, 0.5 g of a powder of molecular sieves 4A (manufactured by Aldrich Co.) was placed in a 25-ml flask, and the air in the flask was thoroughly displaced by argon. 5 ml of methylene chloride was added thereto, and 0.33 ml (0.1 mmole) of the above-prepared diisopropoxydichlorotitanium toluene solution and 28.6 mg (0.1 mmole) of (R)-binaphthol were further added. The mixture was stirred at room temperature for 1 hour, thereby preparing an (R)-binaphtholdichlorotitanium complex.

The above-obtained solution was cooled to $-70°$ C. in a dry ice-acetone bath. To this solution were successively added 88 mg (1 mmole) of methyl glyoxylate and 0.168 g (2 mmole) of 1-methoxy-1,3-butadiene. Reaction was then allowed to proceed at $-30°$ C. for 3 hours, and 10 ml of a sodium hydrogencarbonate aqueous solution was added to the reaction mixture to terminate the reaction. This reaction mixture was filtered through Celite and then subjected to extraction once with a 20 ml of diethyl ether and twice with 20 ml of ethyl acetate. The extract was dried over anhydrous magnesium sulfate. Thereafter, the solvent was removed by evaporation, and the residue was purified by silica gel column chromatography (200 mesh; developing solvent: hexane/ethyl acetate=10/1), thereby obtaining 0.12 g of desired optically active 2-methoxy-6-methoxycarbonyl-5,6-dihydropyran (yield: 79%).

$^1$H-NMR analysis revealed that the ratio of the cis-isomer to the trans-isomer yielded was 78:22.

$^1$H-NMR (CDCl$_3$) δppm:

Cis-isomer: 2.3–2.6 (m, 1H), 3.49 (s, 3H), 3.77 (s, 3H), 4.41 (t, J=6.0 Hz, 1H), 5.03 (m, 1H), 5.69 (m, 1H), 6.04 (m, 1H)

Trans-isomer: 2.3–2.4 (m, 1H), 3.46 (s, 3H), 3.81 (s, 3H), 4.52 (dd, J=7.4 Hz, J=8.4 Hz, 1H), 4.99 (m, 1H), 5.77 (m, 1H), 6.04 (m, 1H)

The optical purity of the product was determined by $^1$H-NMR analysis using an optically active shifting agent, (+)-Eu(DPPM)$_3$ [(+)-europium(III) tris[di(perfluoro-2-propoxypropionyl)methanate], manufactured by Daiichi Pure Chemicals Co., Ltd.]. As a result, it was found that the optical purities of the cis-isomer and trans-isomer were 94% ee and 90% ee, respectively.

The absolute configuration for the product was determined by first isomerizing the dihydropyran derivative product in methanol by use of hydrochloric acid as a catalyst so that the product had a trans-isomer content of 95%, subsequently converting the ester into an alcohol in diethyl ether by use of lithium aluminum hydride, and then hydrogenating the double bonds by using platinum dioxide in methanol to give trans-6-hydroxymethyl-2-methoxytetrahydropyran, followed by optical rotation measurement. As a result, the optical rotation $[\alpha]^{20}$ of the above compound was found to be $-119.9°$ (c=1.07, solvent: benzene). This found value was compared with the optical rotation $[\alpha]^{20}$ of $+129.7°$ (c=4.3, solvent: benzene) for (2S,6S)-6-hydroxymethyl-2-methoxy-3,4,5,6-tetrahydropyran as described in J. Jurczak et al., *J. Chem. Soc., Chem. Commun.*, pp. 540–542 (1983). Based on the comparison, the trans-isomer and cis-isomer were judged to be a (2R,6R)-isomer and a (2S,6R)-isomer, respectively.

EXAMPLE 2

In the same manner as in Example 1, a solution of an (R)-binaphthol-dichlorotitanium complex was obtained. This solution was cooled to $-70°$ C. in a dry ice-acetone bath. To this solution were successively added 88 mg (1 mmole) of methyl glyoxylate and 136 mg (2 mmole) of 2-methyl-1,3-butadiene. Reaction was then allowed to proceed at $-30°$ C. for 3 hours, and 10 ml of a sodiumhydrogen carbonate aqueous solution was added to the reaction mixture to terminate the reaction. The reaction mixture was filtered through Celite and then subjected to extraction once with a 20 ml of diethyl ether and twice with 20 ml of ethyl acetate. The extract was dried over anhydrous magnesium sulfate. Thereafter, the solvent was removed by evaporation, and the residue was purified by silica gel column chromatography (200 mesh; developing solvent: hexane/ethyl acetate=10/1), thereby obtaining 34 mg of desired optically active (6R)-6-methoxycarbonyl-4-methyl-5,6-dihydropyran (yield: 22%).

$^1$H-NMR (CDCl$_3$) δppm: 1.71 (s, 3H), 2.19 (dd, J=16.5 Hz, J=4.1 Hz, 1H), 2.28 (dd, J=16.5 Hz, J=9.6 Hz, 1 H), 3.77 (s, 3H), 4.18 (d, J=16.0 Hz, 1 H), 4.20 (dd, J=4.1 Hz, J=9.6 Hz, 1 H), 4.31

(d, J=16.0 Hz, 1H), 5.41 (m, 1H)

Optical purity: 96% ee

EXAMPLE 3

In the same manner as in Example 1, a solution of an (R)-binaphthol-dichlorotitanium complex was obtained. This solution was cooled to $-70°$ C. in a dry ice-acetone bath. To this solution were successively added 88 mg (1 mmole) of methyl glyoxylate and 282 mg (2 mmole) of 1-dimethylaminocarbonyloxy-1,3-butadiene. Reaction was then allowed to proceed at $-30°$ C. for 10 hours, and 10 ml of a sodium hydrogencarbonate aqueous solution was added to the reaction mixture to terminate the reaction. This reaction mixture was filtered through Celite and then subjected to extraction once with 20 ml of diethyl ether and twice with 20 ml of ethyl acetate. The extract was dried over anhydrous magnesium sulfate. Thereafter, the solvent was removed by evaporation, and the residue was purified by silica gel column chromatography (200 mesh; developing solvent: hexane/ethyl acetate=10/1), thereby obtaining 82 mg of desired optically active 6-methoxycarbonyl-2-dimethylaminocarbonyloxy-5,6-dihydropyran (yield: 36%).

The $^1$H-NMR analysis revealed that the ratio of the cis-isomer to the trans-isomer yielded was 97:3.

$^1$H-NMR (CDCl$_3$) δ ppm:

Cis-isomer: 2.91 (s, 3H), 2.93 (s, 3H), 2.97 (m, 2H), 3.79 (s, 3H), 4.51 (dd, J=5.0 Hz, J=10.1 Hz, 1 H), 5.80 (m, 1 H), 6.11 (m, 1H), 6.36 (m, 1H)

Trans-isomer: 2.91 (s, 3H), 2.93 (s, 3H), 2.97 (m, 2H), 3.79 (s, 3H), 4.65 (m, 1H), 5.80 (m, 1H), 6.11 (m, 1H), 6.36 (m, 1H)

Optical purity;

Cis-isomer (2S,6R): 88% ee

Trans-isomer: unmeasurable due to very low yield

EXAMPLE 4

In the same manner as in Example 1, a solution of an (R)-binaphthol-dichlorotitanium complex was obtained. This solution was cooled to −70° C. in a dry ice-acetone bath. To this solution were successively added 88 mg (1 mmole) of methyl glyoxylate and 196 mg (2 mmole) of 1-methoxy-1,3-pentadiene. Reaction was then allowed to proceed at −10° C. for 1 hour, and 10 ml of a sodium hydrogencarbonate aqueous solution was added to the reaction mixture to terminate the reaction. This reaction mixture was filtered through Celite and then subjected to extraction once with 20 ml of diethyl ether and twice with 20 ml of ethyl acetate. The extract was dried over anhydrous magnesium sulfate. Thereafter, the solvent was removed by evaporation, and the residue was purified by silica gel column chromatography (200 mesh; developing solvent: hexane/ethyl acetate =10/1), thereby obtaining 0.23 g of desired optically active 2-methoxy-6-methoxycarbonyl-5-methyl-5,6-dihydropyran (yield: 63%).

The $^1$H-NMR analysis revealed that the ratio of the endo-isomer to the exo-isomer yielded was 97:3.

$^1$H-NMR (CDCl$_3$) δppm:

Endo-isomer (2S,5S,6R): 1.04 (d, J=6.8 Hz, 3H), 2.25 (m, 1H), 3.53 (s, 3H), 3.79 (s, 3H), 4.43 (d, J=3.6 Hz, 1H), 5.16 (bs, 1H), 5.62 (m, 1H), 6.02 (m, 1H)

Exo-isomer (2R,5R,6R): 1.05 (d, J=7.2 Hz, 3 H), 2.55 (m, 1H), 3.45 (s, 3H), 3.82 (s, 3H), 4.09 (d, J=10.4 Hz, 1H), 4.95 (m, 1H), 5.73 (m, 1H), 5.81 (m, 1 H)

Optical purity:

Endo-isomer (2S,5S,6R): 90% ee

Exo-isomer: unmeasurable due to very low yield

Optical rotation: $[\alpha]_D^{30} = +163°$ (c=0.285, chloroform)

EXAMPLE 5

In the same manner as in Example 1, a solution of an (R)-binaphthol-dichlorotitanium complex was obtained. This solution was cooled to −70° C. in a dry ice-acetone bath. To this solution were successively added 88 mg (1 mmole) of methyl glyoxylate and 224 mg (2 mmole) of 1-methoxy-2-methyl-1,3-pentadiene. Reaction was then allowed to proceed at −30° C. for 1 hour, and 10 ml of a sodium hydrogencarbonate aqueous solution was added to the reaction mixture to terminate the reaction. This reaction mixture was filtered through Celite and then subjected to extraction once with 20 ml of diethyl ether and twice with 20 ml of ethyl acetate. The extract was dried over anhydrous magnesium sulfate. Thereafter, the solvents were removed by evaporation, and the residue was purified by silica gel column chromatography (200 mesh; developing solvent: hexane/ethyl acetate=10/1), thereby obtaining 108 mg of desired optically active 2-methoxy-6-methoxycarbonyl-3,5-dimethyl-5,6-dihydropyran (yield: 54%).

The $^1$H-NMR analysis revealed that the ratio of the endo-isomer to the exo-isomer yielded was 98:2.

$^1$H-NMR (CDCl$_3$) δppm:

Endo-isomer (2S, 5S, 6R): 1.01 (d, J=7.0 Hz, 3H), 1.66 (m, 3 H), 2.46 (m, 1H), 3.48 (s, 3H), 3.78 (s, 3H), 4.38 (d, J=3.5 Hz, 1H), 5.04 (m, 1H), 5.73 (m, 1H)

Exo-isomer (2R, 5R, 6R): 1.02 (d, J=7.1 Hz, 3H), 1.72 (m, 3H), 2.51 (m, 1H), 3.46 (s, 3H), 3.81 (s, 3H), 4.03 (d, J=10.5 Hz, 1H), 4.73 (m, 1H), 5.43 (m, 1H)

Optical purity:

Endo-isomer (2S, 5S, 6R): 88% ee

Exo-isomer: unmeasurable due to very low yield

EXAMPLE 6

In the same manner as in Example 1, a solution of an (R)-binaphthol-dicholorotitanium complex was obtained. This solution was cooled to −70° C. in a dry ice-acetone bath. To this solution were successively added 88 mg (1 mmole) of methyl glyoxylate and 220 mg (2 mmole) of 3-ethylene-4,5-dihydropyran. Reaction was then allowed to proceed at −30° C. for 3 hours, and 10 ml of a sodium hydrogencarbonate aqueous solution was added to the reaction mixture to terminate the reaction. This reaction mixture was filtered through Celite and then subjected to extraction once with 20 ml of diethyl ether and twice with 20 ml of ethyl acetate. The extract was dried over anhydrous magnesium sulfate. Thereafter, the solvent was removed by evaporation, and the residue was purified by silica gel column chromatography (200 mesh; developing solvent: hexane/ethyl acetate=10/1), thereby obtaining 123 mg of desired optically active methyl 3,6,7,8a-tetrahydro-2H, 5H-pyrano[2,3-b]pyran-2-carboxylate (yield: 62%).

The $^1$H-NMR analysis revealed that the ratio of the cis-isomer to the trans-isomer yielded was 89:11.

$^1$H-NMR (CDCl$_3$) δppm:

Cis-isomer (2R, 8aS): 1.68 (m, 2H), 2.33 (m, 4H), 3.63 (m, 1H), 3.78 (s, 3H), 4.06 (m, 1H), 4.38 (dd, J=4.4 Hz, J=9.2 Hz, 1H), 5.14 (br, s, 1H), 5.64 (m, 1 H)

Trans-isomer (2R, 8aR): 1.68 (m, 2H), 2.33 (m, 4H), 3.65 (m, 1H), 3.79 (s, 3H), 4.06 (m, 1H), 4.47 (dd, J=7.0 Hz, J=8.2 Hz, 1H), 4.98 (br, s, 1H), 5.64 (m, 1H)

Optical purity:

Cis-isomer (2R, 8aS): 86% ee

Trans-isomer: unmeasurable due to very low yield

While the invention has been described in detail and with reference to specific embodiments thereof, it will be apparent to one skilled in the art that various changes and modifications can be made therein without departing from the spirit and scope thereof.

What is claimed is:

1. A process for producing an optically active dihydropyran derivative represented by formula (1):

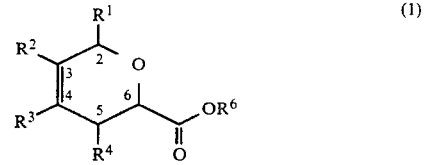

wherein $R^1$, $R^2$, $R^3$, and $R^4$ each represents a hydrogen atom, a lower alkyl group, a tri-lower alkylsilylmethyl group, a lower alkoxycarbonylamino group, or an —$OR^5$ group, wherein $R^5$ represents a lower alkyl group, a lower acyl group, a lower alkoxycarbonyl group, a di-lower alkylcarbamoyl group, or a tri-lower alkylsilyl group, or $R^1$ and $R^2$ are taken together to form a 5- to 7-membered cyclic hydrocarbon group or to form a condensed heterocyclic group with an oxygen atom, or $R^2$ and $R^3$ are taken together to form a 5- to 7-membered cyclic hydrocarbon group or to form a condensed heterocyclic group with an oxygen atom, provided that all of $R^1$, $R^2$, $R^3$, and $R^4$ do not represent hydrogen atoms at the same time; and $R^6$ represents a lower alkyl group, which comprises reacting a diene compound represented by formula (2):

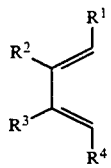

wherein $R^1$, $R^2$, $R^3$, and $R^4$ have the same meanings as defined above, with a glyoxylic acid ester represented by formula (3):

wherein $R^6$ has the same meaning as defined above, in the presence of an optically active binaphthol-titanium complex represented by formula (4):

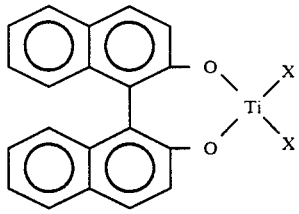

wherein X represents a chlorine atom or a bromine atom.

2. A process as in claim 1, wherein said optically active binaphthol-titanium complex represented by formula (4) is used in an amount of from 0.001 to 1 mole per mole of said diene compound represented by formula (2) and said glyoxylic acid ester represented by formula (3).

3. A process as in claim 1, wherein said optically active binaphthol-titanium complex represented by formula (4) is used in an amount of from 0.01 to 0.1 mole per mole of said diene compound represented by formula (2) and said glyoxylic acid ester represented by formula (3).

* * * * *